United States Patent
Ebi

(10) Patent No.: US 6,868,711 B2
(45) Date of Patent: Mar. 22, 2005

(54) METHOD FOR MONITORING MECHANICAL WEAR

(75) Inventor: Günter Ebi, Hohentengen (DE)

(73) Assignee: Sensoplan Aktiengesellschaft, Hohentengen (DE)

(*) Notice: Subject to any disclaimer, the term of this patent is extended or adjusted under 35 U.S.C. 154(b) by 0 days.

(21) Appl. No.: 10/143,546

(22) Filed: May 10, 2002

(65) Prior Publication Data
US 2003/0209052 A1 Nov. 13, 2003

(51) Int. Cl.[7] ................................................ G01N 3/56
(52) U.S. Cl. ...................................................... 73/7
(58) Field of Search ........................... 356/237.2; 451/6; 73/7; 340/682; 385/138

(56) References Cited

U.S. PATENT DOCUMENTS

| | | | | |
|---|---|---|---|---|
| 4,420,253 A | * | 12/1983 | Pryor ....................... 356/237.1 |
| 4,532,499 A | * | 7/1985 | Collin et al. ................. 340/644 |
| 4,884,434 A | * | 12/1989 | Satake et al. ..................... 73/7 |
| 5,438,860 A | * | 8/1995 | Kawai et al. ..................... 73/7 |
| 5,588,086 A | * | 12/1996 | Fan ............................. 385/138 |
| 6,080,982 A | * | 6/2000 | Cohen .................... 250/227.11 |
| 6,434,512 B1 | * | 8/2002 | Discenzo .................... 702/184 |
| 6,580,511 B1 | * | 6/2003 | Discenzo .................... 356/477 |

FOREIGN PATENT DOCUMENTS

| JP | 01038629 A | * | 2/1989 | ............ G01N/3/56 |
|---|---|---|---|---|
| JP | 01110207 A | * | 4/1989 | ............ G01B/21/00 |

* cited by examiner

Primary Examiner—Charles D Garber
(74) Attorney, Agent, or Firm—Gudrun E. Huckett

(57) ABSTRACT

In a method for monitoring mechanical wear caused by a first component on a second component, wherein the first and second components are movable relative to one another and wherein the first and second component are at least at times in mechanical contact with one another, at least one sensor head is arranged in a wear area to be monitored of the second component. The at least one sensor head is mechanically worn by the first component upon reaching a predetermined wear limit. When the at least one sensor head is mechanically worn, a measuring signal is generated by the at least one sensor head or a change of a measuring signal, produced by the at least one sensor head prior to having been mechanically worn, is detected.

4 Claims, 4 Drawing Sheets

METHOD FOR MONITORING MECHANICAL WEAR

BACKGROUND OF THE INVENTION

1. Field of the Invention

The invention relates to a method for monitoring mechanical wear caused by a first component on a second component, wherein the two components are movable relative to one another and wherein the two components are in mechanical contact at least part of the time.

2. Description of the Related Art

In technical applications it happens that two components are moved relative to one another and that one of the components is subjected to gradual wear. Since this wear can advance to such an extent that the entire device becomes defective, it is necessary to monitor the wear in order to be able to carry out repairs at a predetermined wear limit.

A special field of application of the monitoring device according to the invention is bearing wear of marine propellers. The shaft of the marine propellers is guided in a bushing or a guide bearing. Lubrication of the bearing is realized not by means of special lubricants such as oil or grease but, instead, the lubricant is the water surrounding the bearing which, in the case of ocean-going vessels, is salt water. However, this medium is aggressive with regard to the detectors so that the use of conventional methods for monitoring the wear state of the bushing, for example, by employing distance sensors, is not possible in the case of salt water. For this reason, it has not been possible in the past to perform monitoring of wear in such aggressive environments.

In general, the wear monitoring method according to the invention is provided for monitoring the wear state, in particular, in the presence of aggressive media.

SUMMARY OF THE INVENTION

It is an object of the present invention to provide a simple method of the aforementioned kind for monitoring wear.

In accordance with the present invention, this is achieved in that a sensor head is arranged in the wear area to be monitored of the second component, in that this sensor head has correlated therewith a measuring signal, in that the sensor head is mechanically worn by means of the first component upon reaching a predetermined wear limit, and in that in this way a measuring signal is generated or a measuring signal is changed and the change is detected.

The principal idea of the wear monitoring method according to the invention resides in a specially configured sensor head. This sensor head, in the original state, i.e., before the wear limit is reached, can be encapsulated such that a possibly present aggressive medium surrounding it will not affect its function. The basic principle of the invention resides in that, upon reaching a predetermined wear limit, the sensor head or corresponding sensor elements are mechanically destroyed and that, based on this, a measuring signal is derived which is measured and is understood to indicate that the wear limit has been reached. The system is characterized as a whole in that it is comprised of only a few parts, is safe and operates reliably and, moreover, is inexpensive. Moreover, it is also possible without problems to exchange the sensor head for another.

Preferably, the first component is movable and the second component is stationary. An example for this is the aforementioned shaft of a marine propeller. Basically, it is also conceivable that both components are movable. In this case, it is required that the measuring signals of the sensor (rotating with the respective component) is transmitted onto a stationary unit.

Advantageously, the wear progression can be monitored by means of a staggered arrangement of several sensor heads. This provides a very safe method enabling a continuous monitoring of the critical components. By providing several sensor elements with correspondingly configured sensor heads, it is also possible to provide redundance.

A first technical realization of the sensor according to the invention provides an optical system using one or several fiber optic cables. This optical monitoring of the wear has the great advantage that it can be realized also in aggressive as well as explosive environments because within this critical wear area there are no electrical voltages present. In this way, a very safe system is provided. Laser light of low energy can be as a signal carrier. In this way, no electrical signals or contacts are present within the housing. The basic principle of the sensor system is that, upon reaching the wear limit, the metal coating is simultaneously removed so that no reflection of the introduced light can occur anymore at the tip of the light guide. This results in a significant signal drop at the light receiver. A further advantage of this method is that it is independent of the temperature, the pressure as well as the composition of the involved materials. Moreover, this method can be universally applied.

According to the invention, the front end of the light guide can be provided with a protective sleeve which is comprised, for example, of titanium. In this way, the tip of the light guide is sealed hermetically relative to the environment. The light guide can additionally be surrounded within the sleeve by a glass capillary. This glass capillary than secures the light guide in a fixed and stable position within the protective sleeve.

A further development of the invention concerns supplying the light signals from the exterior of the housing to the sensor head and receiving the reflected light signals as measuring signals external to the housing. A light-transmissive element is provided in the housing, i.e., a transparent glass pane, and provides an interface between the interior of the housing and the exterior area of the housing. The advantage is that in this way a possibility is realized of providing all electrical or electronic elements outside of the housing while still a proper transmission of the light pulses into the interior of the housing is ensured. This provides a safe and solid interface system. As a material for the light-transmissive or transparent element a material should be selected which is resistant with respect to possibly present aggressive media.

A second embodiment of the sensor system according to the invention resides in that a closed gas system is provided which has a certain pressure (over pressure or under pressure) wherein the magnitude of the pressure is continuously measured as a measuring signal. The pressure in the gas pressure line must be different from the surrounding pressure so that a pressure change can be detected as a change of the measuring signal. This second variant is also characterized by a simple technical configuration. Moreover, it is technically also possible to guide the gas pressure line through the housing wall. This method is also suitable for surrounding media in which no electrical voltage should be present.

The third embodiment of the sensor system resides in that the wear of the sensor head interrupts an electrical circuit, wherein a measuring signal in the form of electric current is provided and the resulting current drop is detected (change of the measuring signal). In this case, the sensor head is also encapsulated by a corresponding protective sleeve relative to the surroundings.

A fourth embodiment of the sensor system provides a spring element which is tensioned in its original mounted state. By destroying the suspension or anchoring of the spring element, the spring element will then move into its rest position. This movement or the resulting end (rest) position of the spring element can then be detected. Accordingly, a mechanical/magnetic sensor, an electric/magnetic sensor or an electric/mechanical/magnetic sensor can be realized technically, for example, in that the change of a magnetic field caused by the movement of the spring element is measured or in that the end position of the spring element actuates an electric contact.

DESCRIPTION OF THE PREFERRED EMBODIMENTS

Figure 1:
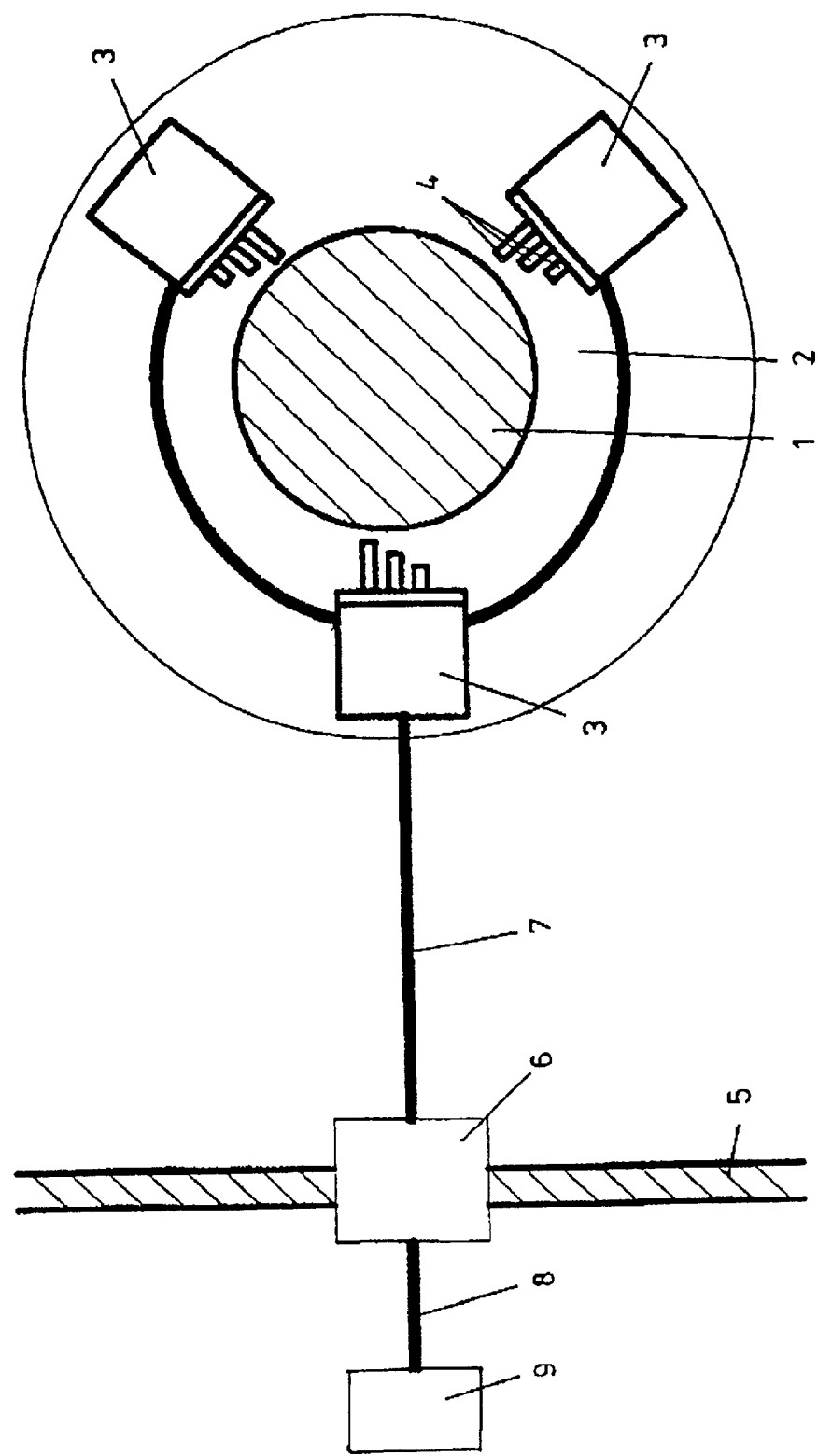
FIG. 1 is a schematic view of the basic principle of the wear monitoring system according to the invention.
Figure 2:
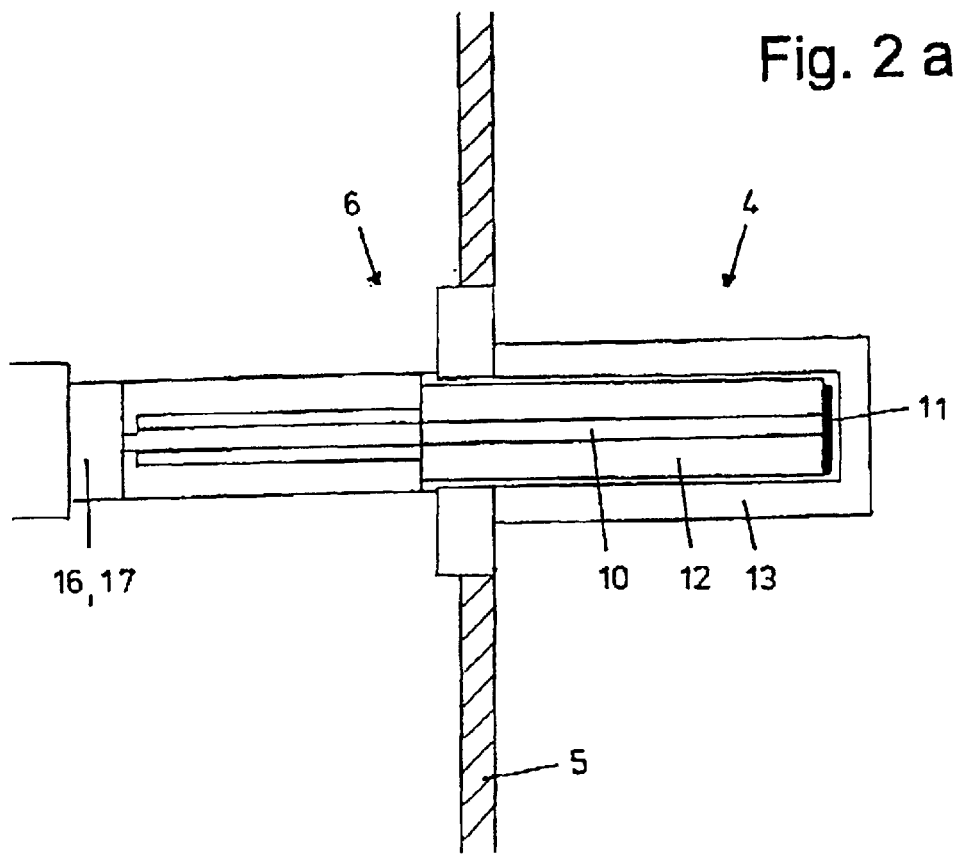
FIG. 2a shows a first embodiment of the sensor system using a light guide.
FIG. 2b shows in connection with the first embodiment and arrangement for the passage of the light signals through the wall of the housing.
Figure 2:
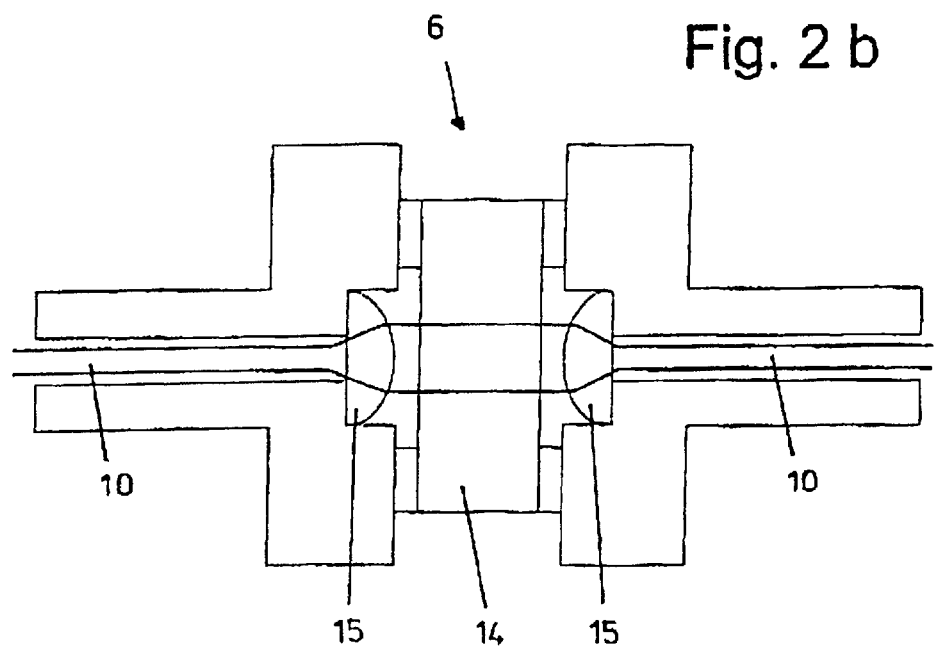

The basic principle of the wear monitoring system according to the invention is illustrated in FIG. 1. A first component 1 in the form of a shaft is provided. This first component 1 is rotatably supported in a second component 2, which is a bearing for the shaft.

In the second component 2 a total of three sensor elements 3 are arranged each comprising three sensor heads 4. These three sensor elements 3 are connected with one another. As illustrated in the drawing, the sensor heads 4 are staggered radially relative to the first component 1 to provide a graduated wear limit.

Moreover, FIG. 1 shows the wall of the housing 5. In this housing 5 a so-called interface 6 is arranged which connects the signal line 7 in the interior of the housing 5 with the signal line 8 outside of the housing 5 and thus with a corresponding electronic unit 9.

The abstract, general principle of the function of the described wear monitoring device is as follows.

A first component 1 in the form of a shaft rotates in the second component 2. Over the course of time, the inner bore of the second component 2 will widen as a result of wear so that the second component 2 becomes defective gradually and the first component 1 is no longer property supported. This wear progression is monitored.

The widening of the bore or opening in the second component 2 causes the successive wear of the sensor heads 4 and finally their destruction. The sensor heads 4 are configured such that the destruction results in a change of the measuring signal or the generation of a measuring signal. The measuring signal which is generated or the change of the measuring signal is transmitted by means of signal lines 7, 8 to the electronic unit 9 and is processed therein.

The concrete technical realizations of the sensor principle is described in connection with the embodiments of FIGS. 2 through 5.

In the embodiment of the sensor system according to FIG. 2a, a light guide 10 is connected to the sensor head 4. This light guide 10 has at its forward end a metal coating 11. The light guide 10 is surrounded in the area of the sensor head 4 by a stabilizing sleeve 12 as well as a protective sleeve 13 which is closed at the front end.

The light guide 10 passes through the housing 5 by means of a light-transmissive element (transparent element) 14 arranged in a seal-tight way in the housing 5. The portion of the light guide 10 in the interior of the housing 5 is connected to a focusing lens 15. The portion of the light guide 10 outside of the housing 5 is also connected to a corresponding focusing lens 15.

The function of this embodiment is as follows.

A light sending unit 16 arranged outside the housing 5 sends laser light pulses. The laser light pulses are guided via the focusing lens 15 and the transparent element 14 into the light guide 10 in the interior of the housing 5. The metal coating 11 reflects the light pulses so that they are received in a light receiver 17. As a result of the gradual wear of the second component 2, which wear reaches also the sensor head 4, the protective sleeve 13 and subsequently the metal coating 11 are removed. This causes at least a significantly decreased reflection of the light which is detected by the light receiver 17.

Figure 3:
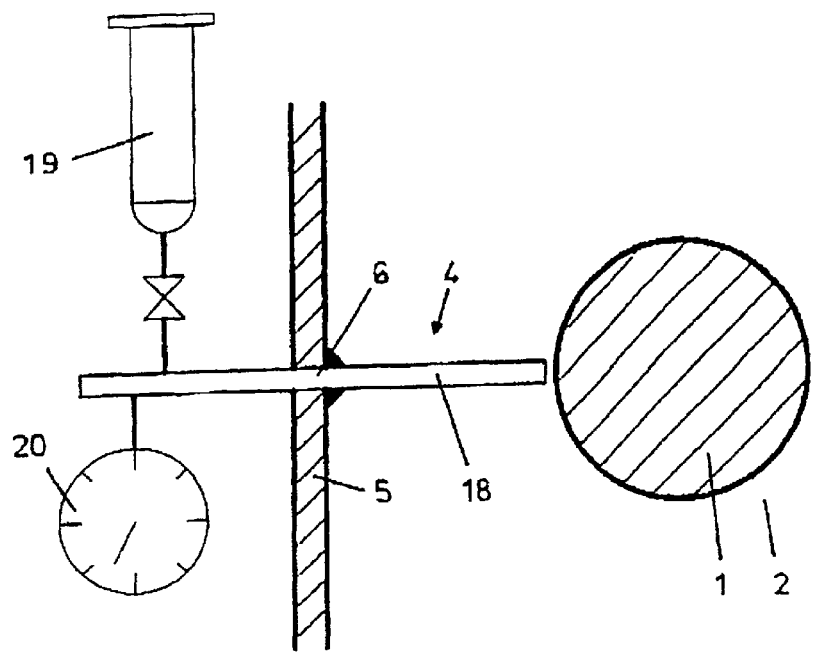
FIG. 3 is a second embodiment of the sensor system using a gas pressure line.

In the embodiment of FIG. 3, a gas pressure line 18 is provided which is guided through the housing 5. The gas pressure line 18 is connected to a gas supply 19 as well as a pressure gauge 20.

The function of this embodiment is as follows.

The gas pressure line 18 has a predetermined certain inner pressure. The destruction of the sensor head 4 causes the gas pressure line 18 to leak and thus results in a pressure change which is measured by the pressure gauge 20.

Figure 4:
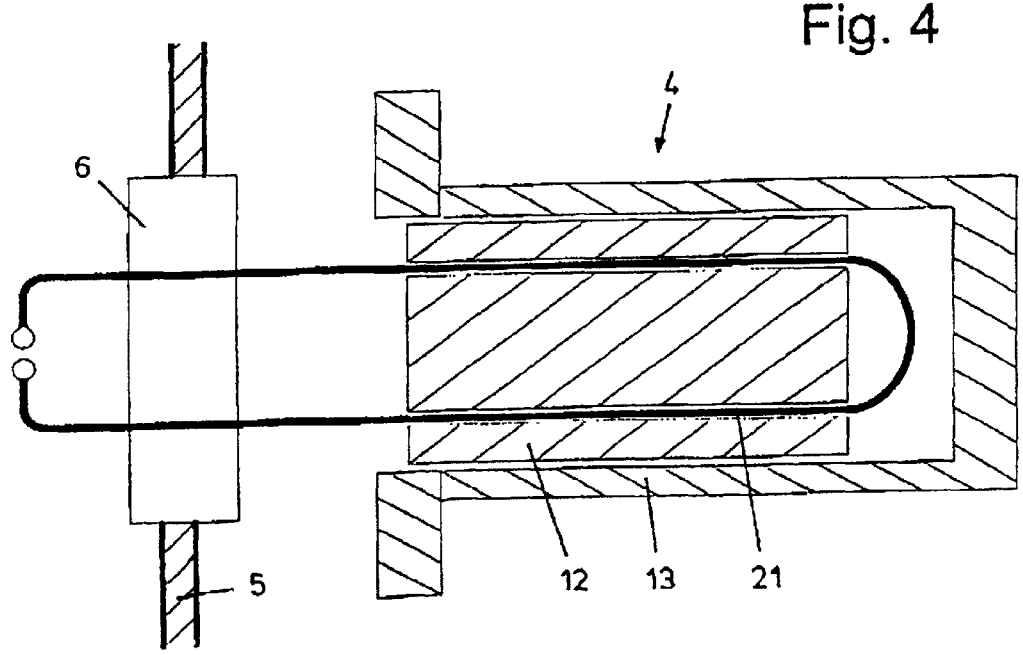
FIG. 4 shows a third embodiment of the sensor system employing an electrical circuit.

The embodiment of the sensor system of FIG. 4 provides an electrical line 21 which is encapsulated correspondingly by a protective sleeve 13 in the interior of the housing 5. The electrical lines 21 are guided through a window in the housing 5 to the exterior.

The function of this embodiment is as follows.

The wear of the sensor head 4 destroys the electrical line 21 in this area and, accordingly, the electrical circuit is interrupted. The resulting current drop is measured outside of the housing 5 with a corresponding measuring instrument.

Figure 5:
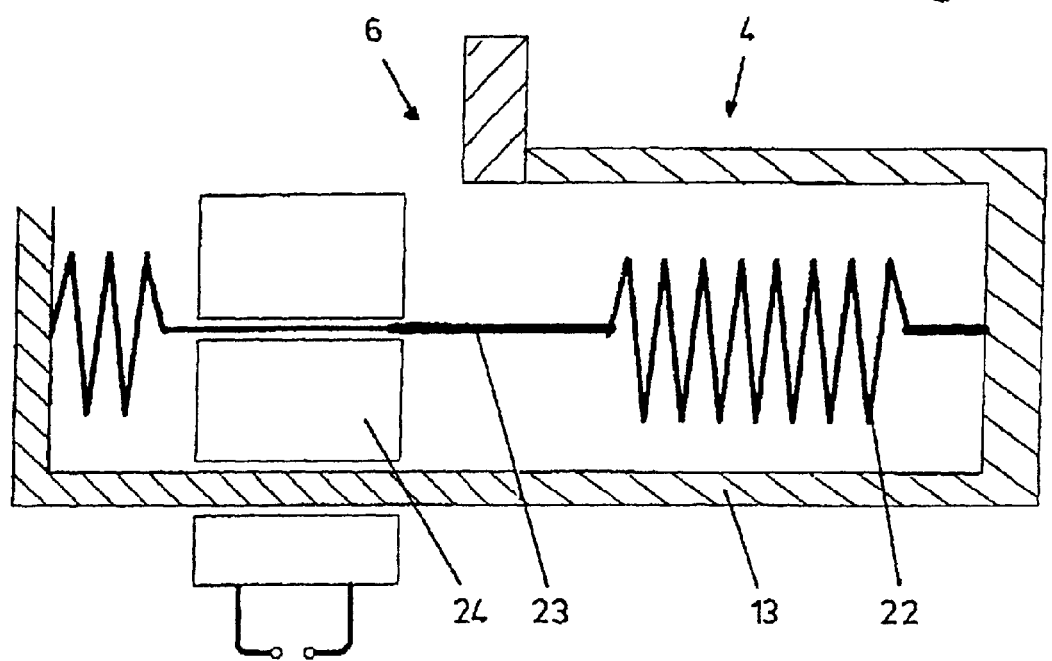
FIG. 5 shows a fourth embodiment of the sensor system using a spring element in connection with a magnetic detector.

The fourth embodiment according to FIG. 5 has a spring element 22 in the form of a tension spring. It is anchored with its forward end in a protective sleeve 13. In the rearward area of the spring element 22 a metallic core 23 is provided which is surrounded by a solenoid 24.

The function of this embodiment is as follows.

The destruction of the sensor head 4 destroys the suspension or attachment of the spring element 22 in the protective sleeve 13 so that the spring element 22 is restored into its rest position, i.e., it moves to the left in the drawing. As a result of the core 23 penetrating the solenoid 24, a voltage is induced which is measured.

While specific embodiments of the invention have been shown and described in detail to illustrate the inventive principles, it will be understood that the invention may be embodied otherwise without departing from such principles.

What is claimed is:

1. A method for monitoring mechanical wear caused by a first component (1) on a second component (2), wherein the first component (1) is movable relative to the stationary second component (2) and wherein the first and second components (1,2) are at least at times in mechanical contact with a another, the method comprising the steps of:

arranging at least one sensor head (4) in a wear area to be monitored of the second component (2);

connecting a light guide (10) to the at least one sensor head (4), wherein the light guide (10) has a forward end with a metal coating (11);

guiding a measuring signal in the form of light into the light guide (10) and reflecting the light on the metal coating (11);

causing the metal coating (11) to be mechanically worn by the first component (1) upon reaching a predetermined wear limit;

measuring an intensity of the light reflected on the metal coating (11); and dectecting a drop in the Intensity of the light reflected on the metal coating (11) when the predetermined wear limit is reached.

2. The method according to claim 1, wherein several of the at least one sensor heads (4) are arranged in a staggered arrangement so that the wear limit is graduated.

3. The method according to claim 1, wherein the forward end of the light guide (10) is surrounded by a protective sleeve (13).

4. The method according to claim 1, further comprising the steps of;

providing a closed housing (5) and arranging the first and the second components (1,2) in the interior of the housing (5);

arranging a light sending unit (16) and a light receiver (17) outside of the housing (5), wherein the housing (5) has a light-transmissive element (14) and wherein the light guide (10) is comprised of a first portion outside the housing (5) and a second portion in the Interior of the housing (5), and wherein the first and second portions are connected to the light-transmissive element (14).

* * * * *